(12) United States Patent
Leone et al.

(10) Patent No.: US 10,953,115 B2
(45) Date of Patent: Mar. 23, 2021

(54) PRODUCTION OF STERILE ACTIVE PHARMACEUTICAL INGREDIENTS

(75) Inventors: Mario Leone, Casalmaiocco (IT); Pierfrancesco Morosini, Mapello (IT)

(73) Assignee: Icrom S.R.L., Concorezzo (IT)

( * ) Notice: Subject to any disclaimer, the term of this patent is extended or adjusted under 35 U.S.C. 154(b) by 1307 days.

(21) Appl. No.: 14/398,912

(22) PCT Filed: May 9, 2012

(86) PCT No.: PCT/IT2012/000136
§ 371 (c)(1),
(2), (4) Date: Jan. 13, 2015

(87) PCT Pub. No.: WO2013/168186
PCT Pub. Date: Nov. 14, 2013

(65) Prior Publication Data
US 2015/0141412 A1    May 21, 2015

(51) Int. Cl.
*A61L 2/00* (2006.01)
*A61K 31/542* (2006.01)

(52) U.S. Cl.
CPC .......... *A61L 2/0035* (2013.01); *A61K 31/542* (2013.01)

(58) Field of Classification Search
CPC ........................... A61K 31/542; A61L 2/0035
See application file for complete search history.

(56) References Cited

U.S. PATENT DOCUMENTS

2009/0258850 A1* 10/2009 Frincke ............... A61K 9/0019 514/182

FOREIGN PATENT DOCUMENTS

| | | |
|---|---|---|
| EP | 941094 A1 | 9/1999 |
| EP | 2394637 A1 | 12/2011 |
| GB | 1274409 A | 5/1972 |
| WO | WO-199825620 A1 | 6/1998 |
| WO | WO-03026703 A1 | 4/2003 |
| WO | WO-2006124988 A2 | 11/2006 |
| WO | WO-2007129961 A1 | 11/2007 |
| WO | WO-2008081166 A1 | 7/2008 |

OTHER PUBLICATIONS

Pharmaceutical Technology Editors, "Radiation Sterilization of Parenterals", PharmTech, May 1, 2007, vol. 2007 Supplement, Issue 2 (Year: 2007).*
Fengmei et al., "Evaluation of plastic packaging materials used in radiation sterilized medical products and food", Radiation Physics and Chemistry, 2000, vol. 57, pp. 435-439 (Year: 2000).*
Jacobs, "A Review of the Effects of Gamma Radiation on Pharmaceutical Materials", J. Biomaterials Applications, 1995, vol. 10, pp. 59-96 (Year: 1995).*
Phillips, "Radiation technology in surgery and the pharmaceutical industry: An overview of applications", IAEA Bulletin, 1994, pp. 19-23 (Year: 1994).*
U.S. Pharmacopoeia Convention; "<1211> Sterilization and Sterility Assurance of Compendial Articles," United States Pharmacopeia (USP), 2014, 8 pages.
European Directorate for the Quality of Medicines & Healthcare (EDQM), "5.1. General Texts on Sterility: 5.1.1. Methods of Preparation of Sterile Products," European Pharmacopoeia 5.0, Jan. 2005, pp. 445-447.
Association for the Advancement of Medical Instrumentation (AAMI), "Sterilization of Health Care Products—Radiation—Part 1: Requirements for Development, Validation, and Routine Control of a Sterilization Process for Medical Devices," American National Standard, 2006, 16 pages.
Tsuda, Kyosuke, et al.; "Pharmaceutical Engineering: Development of Pharmaceutical Products Basis Course X"; 1971, First Edition; pp. 404-405.
Sekiguchi, Masayuki; "Problems in Introducing Radiation Sterilization to Parenterals"; Radiation Application Technological Database Data No. 010055; http://www.rada.or.jp/database/home4/normal/ht-docs/member/synopsis/010055.html; Nov. 9, 2007; 9 pages.
European Commission, Enterprise and Industry; "Use of Ionising Radiation in the Manufacture of Medicinal Products"; EC-GMP Guide, Annex 12; 2004; pp. 115-120.
Fischer, Michael, "International Search Report," prepared for PCT/IT2012/000136, dated Mar. 19, 2013, six pages.
U.S. Pharmacopoeia Convention; "<1211> Sterilization and Sterility Assurance of Compendial Articles," United States Pharmacopeia (USP), 2012, 8 pages.

* cited by examiner

*Primary Examiner* — James D. Anderson
(74) *Attorney, Agent, or Firm* — Winstead PC

(57) ABSTRACT

The invention refers to a process for preparing sterile active pharmaceutical ingredients (APIs) useful in the preparation of sterile product for ophthalmic use. The process comprises the gamma-ray sterilization treatment of the APIs powder in a protective atmosphere.

6 Claims, No Drawings

PRODUCTION OF STERILE ACTIVE PHARMACEUTICAL INGREDIENTS

FIELD OF THE INVENTION

The present invention refers to a process for preparing sterile drug substances, useful in the preparation of sterile drug product for ophthalmic use.

BACKGROUND OF THE INVENTION

Sterile active pharmaceutical ingredients (APIs) could be manufactured by aseptic processing, that is highly costly for a drug substance considering the low value of the API compared with the final drug formulation, alternatively terminal sterilization is more convenient and cost effective; among those methods Pharmacopoeias recognize 5 procedures (eg US Pharmacopoeia chapter <1211>"sterilization and sterility assurance of compendial articles"): Steam Sterilization, Dry Heat Sterilization, Gas Sterilization (ethylene oxide), Sterilization by Ionizing Radiation (gamma ray, electron beam), Sterilization by Filtration.

No all the methodologies could be suitable for usage with pharmaceutical powders, (generally heat and humidity sensitive), like steam sterilization employing saturated steam under pressure is carried out in a chamber called an autoclave at 120° C. or dry heat sterilization where the unit is operating at not less than 250° C. The most commonly employed method of gaseous sterilization is ethylene oxide. Among the disadvantages of ethylene oxide are its highly flammable nature unless mixed with suitable inert gases, its mutagenic properties, and the possibility of toxic residues in treated materials, particularly those containing chloride ions. One of the principal limiting factors of the ethylene oxide sterilization process is the limited ability of the gas to diffuse to the innermost product areas that require sterilization. Package design and chamber loading patterns therefore must be determined to allow for necessary gas penetration.

The rapid proliferation of medical devices unable to withstand heat sterilization and the concerns about the safety of ethylene oxide have resulted in increasing applications of radiation sterilization. This method may also be applicable to active pharmaceutical ingredients and final dosage forms. The advantages of sterilization by irradiation include low chemical reactivity, low measurable residues, and the fact that there are fewer variables to control. In fact, radiation sterilization is unique in that the basis of control is essentially that of the absorbed radiation dose, which can be precisely measured. Dose-setting and dose-substantiation procedures are typically used to validate the radiation dose required to achieve a sterility assurance level. Irradiation causes only a minimal temperature rise but can affect certain grades and types of plastics and glass.

The two types of ionizing radiation in use are radioisotope decay (gamma radiation) and electron-beam radiation. In either case the radiation dose established to yield the required degree of sterility assurance should be such that, within the range of minimum and maximum doses set, the properties of the article being sterilized are acceptable.

The sterilization of fluids by filtration is a separative process and differs from the other methods of sterilization that rely on destructive mechanisms. Filtration through microbial retentive materials is frequently employed for the sterilization of heat-labile solutions by physical removal of the contained microorganisms. One of the disadvantages of this technique is that it is not applicable on low soluble products, filtration in case of suspensions is not practicable since the filtration pore are very fine (down to 0.2 microns) therefore a very clear solution is required.

Brinzolamide is a carbonic anhydrase inhibitor (specifically, carbonic anhydrase II). Carbonic anhydrase is found primarily in erythrocytes (but also in other tissues including the eye); it is formulated as an ophthalmic suspension (Azopt and Azarga® by Alcon Laboratories) used for the treatment of open-angle glaucoma and raised intraocular pressure due to excess aqueous humor production. It is a known drug substance and a monograph has been published in the USP.

European patent EP 941094 B1 (Alcon Laboratories) describes a manufacturing process for the drug product starting from the non-sterile drug substance stating that conventional sterilization methods cannot be employed in the manufacture of suspensions comprising brinzolamide since the compound recrystallizes at autoclaving temperatures forming large needle-type crystals. According to EP 941094 patent, also dry heat sterilization is not suitable since it causes melting of the material, whereas sterilization by ethylene oxide and gamma irradiation introduces unacceptable degradation products. Sterile filtration is not achievable due to the poor solubility of brinzolamide.

European patent application. EP 2394637 A1 (Zaklady Farmaceutyczne Polpharma) describes a manufacturing process for the brinzolamide ophtalmic suspension, starting from sterile drug substance, the sterilization is claimed to be performed with ethylene oxide or with gamma ray radiation. Sterilization with ethylene oxide is difficult to perform and it is hardly suitable for industrial manufacture of active pharmaceutical ingredients as required by pharmacopoeias and current GMP. Different concerns is related to sterilisation by radiation since there is a dedicated EU GMP guideline on the manufacture of sterile drugs (Annex-12 Use of Ionising Radiation in the Manufacture of Medicinal Products): "[ . . . ] Radiation sterilisation is used mainly for the sterilisation of heat sensitive materials and products. Many medicinal products and some packaging materials are radiation-sensitive, so this method is permissible only when the absence of deleterious effects on the product has been confirmed experimentally"; in particular usage of gamma ray irradiation is provided by Eur. Ph. chapter 5.1.1, where a precise energy is foreseen in order to have the right sterility assurance level (SAL): "[ . . . ] For this method of terminal sterilisation the reference absorbed dose is 25 kGy. Other doses may be used provided that it has satisfactorily been demonstrated that the dose chosen delivers an adequate and reproducible level of lethality when the process is operated routinely within the established tolerances. The procedures and precautions employed are such as to give an SAL of $10^{-6}$ or better".

EP 2394637 overcomes a technical prejudice concerning the sterilization of Brinzolamide (see EP 941094 B1) showing that sterilization by gamma ray radiation can be successfully applied to this product. Particularly, according to EP 2394637 sterilization by gamma irradiation is performed employing any pharmaceutically acceptable dose of gamma irradiation, preferably the dose of either 5, 10, 15 or 25 KG and more preferably the dose of 15 kGy. However EP 2394637 provides no details about the degradation of Brinzolamide active pharmaceutical ingredients, measuring only enantiomeric purity. Considering that the sterility assurance is the key for a industrial manufacturing process of the drug substance even in this case it seems that there is no evidence that this procedure could be suitable for practical purpose.

For all those considerations there is still need of an industrial procedure for the manufacture of Brinzolamide sterile pharmaceutical ingredient useful in the preparation of medicinal products.

The problem which the invention intends to solve is to make available a process for the preparation of brinzolamide sterile grade, which allows to use high energies of irradiation (25 KGy), reducing the degradation phenomena (in agreement with the provisions in force).

SUMMARY OF THE INVENTION

Now the Applicant has surprisingly found that the irradiation with gamma rays, when carried out directly on non-micronized or micronized bulk powder of an active pharmaceutical ingredient (API), preferably Brinzolamide, in the absence of oxygen, does not give rise to degradation processes and allows the physical-chemical characteristics of the products be preserved complying to the US Pharmacopoeia (USP) relevant monograph. Subject of the present invention, is therefore a process for the preparation of a sterile active pharmaceutical ingredients (APIs) powder comprising the gamma-ray sterilization treatment of the APIs in a protective atmosphere. The process according to the invention is conveniently carried out in a suitable container and on Brinzolamide powder.

The protective atmosphere is important in order to prevent degradations due to gamma irradiation, the packaging is also proper designed to maintain the sterility of the powder during its shelf-life.

Features and advantages of the present invention will be illustrated in detail in the following description.

DETAILED DESCRIPTION OF THE INVENTION

The present invention makes it possible to meet the above mentioned requirements thanks to the use of gamma rays for the sterilisation of Brinzolamide, carrying out the process after the micronisation process.

The term "protective atmosphere" refers to any atmosphere that replaces ambient air. suitable protective atmospheres include vacuum, argon, nitrogen, or helium, preferably vacuum, nitrogen or helium atmosphere According to the present process, the sterilisation procedure may be carried out on the powder product packed under vacuum in a suitable container, such as a sealed bag made of a suitable plastic material, preferably polyethylene; this container is in its turn sealed in another bag made of oxygen and humidity proof, "high barrier materials" such us polylaminated aluminium or metallized foil coupled with plastic material such as polyester and polypropylene or polyethylene, to avoid the presence of oxygen and humidity during irradiation and to isolate the sterile material from the external environment in order to keep the initial sterility level.

We found surprising the role of oxygen in the degradation process during sterilization process, since the gamma-ray could promote the activation of molecular oxygen in radical species (singlet-triplet shift) that decompose the brinzolamide molecule. The role of the oxygen is more evident in the micronized powder since the surface area is going to increase dramatically with the decrease of the size of the particles; with the increasing of the surface area there is the increase of the surface exposed to air so the behaviour of the micronised powder is completely different from the behaviour of the non micronised powder and based on the state of the art this was unpredictable. In a preferred embodiment of this invention the protective packaging is performed in modified atmosphere (nitrogen or helium) in order to completely remove oxygen, then material is vacuum sealed. The packaging material has the crucial role to isolate the drug substance from the external environment, so during sterilization process avoid contact with oxygen and after the sterilization process maintain the sterility grade.

The sterilisation step according to the process of the invention was validated according to EU GMP and European Medicines Agency guidelines: "Use of Ionising Radiation in the manufacture of Medicinal Products" Annex 12 and 3AQ4a, taking also in consideration ISO guideline UNI EN ISO 11137-1-2-3: 2006. The validation work guarantee a Sterility Assurance Level (SAL) of at least $10^{-6}$ and the so obtained product is "sterile" according to the criteria of European Pharmacopoeia and US Pharmacopoeia. Gamma ray are produced from Cobalt 60 source, the process applies to micronised or not micronised powder packed in high barrier materials, Brinzolamide is a dry powder complying with the current USP monograph, the terms micronised powder is related to a fine powder with 90% of particle size distribution below 20 micron or less. The drug substance has a low bioburden, typically less than $10^3$ CFU per gram for which the prescribed dose of 25 KGy is suitable to have the required SAL less than $10^{-6}$. The sterilisation process could be performed at ambient temperature or below zero up to $-78°$ C.

It was proved by the Applicant that the present sterilisation procedure, when applied to Brinzolamide in bulk powder form, does not cause significant degradation process or when an increase is observed, it is lower than the prescribed specification of USP test for related substances: not more than 0.3% of single impurity and 1.0% of total sum of impurities; and more in general the resulting sterile product is fully in compliance with all the quality criteria established by US Pharmacopoeia relevant monograph. The sterile active pharmaceutical ingredient (APIs), preferably Brinzolamide, obtained according to the process of the invention are used together with pharmaceutically acceptable carrier for preparing pharmaceutical composition.

The sterile Brinzolamide obtained according to the process of the invention is used together with pharmaceutically acceptable carrier for preparing pharmaceutical composition for the treatment of open-angle glaucoma and raised intraocular pressure.

EXAMPLES

The following examples will further illustrate the present invention without, however limiting it thereto.

All the analysis were performed according to USP Brinzolamide monograph, sterility and bioburden test were performed according to Eur. Ph. and USP.

Two related substances (impurities) are described in the USP monograph: Impurity A and Impurity B.

Impurity A is the enantiomer of Brinzolamide, typically produced upon heating of the drug substance solutions, that is the main degradation product of the process described in the EP 941094 B1, since the sterilization process is performed in autoclave at 120° C.

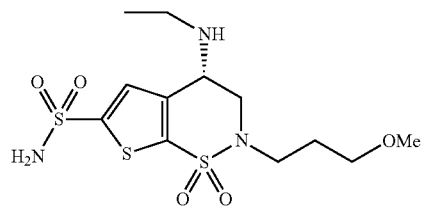 [SMILES: CCN[C@@H]1CN(CCCOC)S(=O)(=O)c2sc(S(N)(=O)=O)cc21]

Impurity A. (S)-4-(Ethylamino)-3,4-dihydro-2-(3-methoxypropyl)-2H-thieno[3,2-e]-1,2-thiazine-6-sulfonamide 1,1-dioxide Impurity B is the des-ethyl analogue of Brinzolamide, typically produced upon UV light stress or under radiation exposure, like gamma ray sterilization process.

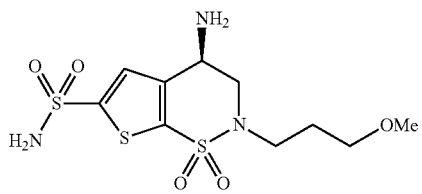 [SMILES: COCCCN1C[C@H](N)c2cc(S(N)(=O)=O)sc2S1(=O)=O]

Impurity B. (R)-4-amino-3,4-dihydro-2-(3-methoxypropyl)-2H-thieno[3,2-e]-1,2-thiazine-6-sulfonamide 1,1-dioxide Other impurities (Impurity C and Impurity D) were commonly found in Brinzolamide drug substances arising from the manufacturing process and/or from the gamma-ray sterilization treatment.

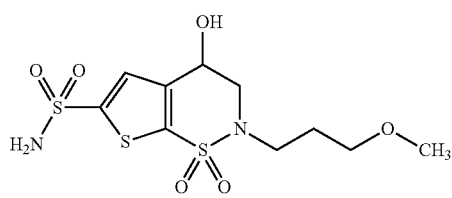 [SMILES: COCCCN1CC(O)c2cc(S(N)(=O)=O)sc2S1(=O)=O]

Impurity C. 4-hydroxy-3,4-dihydro-2-(3-methoxypropyl)-2H-thieno[3,2-e]-1,2-thiazine-6-sulfonamide 1,1-dioxide

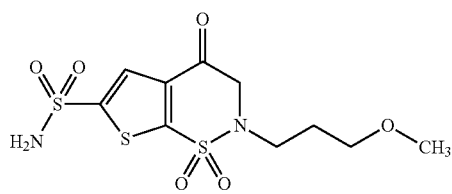 [SMILES: COCCCN1CC(=O)c2cc(S(N)(=O)=O)sc2S1(=O)=O]

Impurity D. 4-oxo-3,4-dihydro-2-(3-methoxypropyl)-2H-thieno[3,2-e]-1,2-thiazine-6-sulfonamide 1,1-dioxide Additional detectable impurities were found typically as degradation byproducts of the gamma ray treatment, they are not considered individually but only as sum of impurities (both known and unknown):

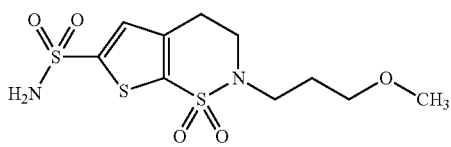 [SMILES: COCCCN1CCc2cc(S(N)(=O)=O)sc2S1(=O)=O]

3,4-dihydro-2-(3-methoxypropyl)-2H-thieno[3,2-e]-1,2-thiazine-6-sulfonamide 1,1 dioxide

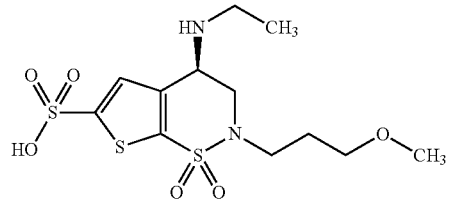 [SMILES: CCN[C@H]1CN(CCCOC)S(=O)(=O)c2sc(S(=O)(=O)O)cc21]

(R)-4-(Ethylamino)-3,4-dihydro-2-(3-methoxypropyl)-2H-thieno[3,2-e]-1,2-thiazine-6-sulfonic acid 1,1-dioxide Example 1

Four Different samples of Brinzolamide USP grade (3 g each not-micronized material), were packed in LDPE liner inside a Barrier Composite Foil (Polyester, Aluminium, HDPE), each package was exposed to different radiation grade: 10, 15, 20 and 25 KGy at room temperature (RT). The material was tested according to USP, details about appearance of the powder, related substances and sterility were given in Table 1.

TABLE 1

| Test | 10 KGy, RT | 15 KGy, RT | 20 KGy, RT | 25 KGy, RT |
|---|---|---|---|---|
| Appearance | White powder | White powder | Greenish powder | Greenish powder |
| Impurity A | Not detected | Not detected | Not detected | Not detected |
| Impurity B | 0.06% | 0.07% | 0.10% | 0.10% |
| Impurity C: | <0.05% | <0.05% | <0.05% | <0.05% |
| Impurity D: | 0.11% | 0.14% | 0.19% | 0.21% |
| Total Impurities | 0.2% | 0.2% | 0.3% | 0.4% |
| Sterility | Sterile | Sterile | Sterile | Sterile |

All the samples complies with the USP specifications apart the appearance of the powder in the 20 and 25 KGy trials.

Example 2

One sample of micronised Brinzolamide (100 g) USP grade was packed in LDPE liner inside a double Barrier Composite Foil (Polyester, Aluminium, HDPE), the material was exposed to a radiation of 25 KGy at room temperature. The material was tested according to USP, details about appearance of the powder, related substances and sterility were given in Table 2.

TABLE 2

| Test | 25 KGy, RT |
|---|---|
| Appearance | Almost White powder |
| Impurity A | Not detected |
| Impurity B | 0.29% |
| Impurity C | <0.05% |
| Impurity D | 0.62% |
| Total Impurities | 1.4% |
| Sterility | Sterile |

The sample does not complies with USP specification

Example 3

One sample of micronised Brinzolamide (100 g) USP grade was packed under vacuum in LDPE liner inside a double Barrier Composite Foil (Polyester, Aluminium, HDPE), the material was exposed to a radiation of 25 KGy at room temperature. The material was tested according to USP, details about appearance of the powder, related substances and sterility were given in Table 3.

TABLE 3

| Test | 25 KGy, RT, under vacuum |
|---|---|
| Appearance | White powder |
| Impurity A | Not detected |
| Impurity B | 0.09% |
| Impurity C | <0.05% |
| Impurity D | 0.30% |
| Total Impurities | 0.6% |
| Sterility | Sterile |

The sample complies with USP specification

Example 4

One sample of micronised Brinzolamide (100 g) USP grade was packed under vacuum and under controlled atmosphere (nitrogen) in LDPE liner inside a double Barrier Composite Foil (Polyester, Aluminium, HDPE), the material was exposed to a radiation of 25 KGy packed in dry ice at −78° C. The material was tested according to USP, details about appearance of the powder, related substances and sterility were given in Table 4.

TABLE 4

| Test | 25 KGy, −78° C., $N_2$, under vacuum |
|---|---|
| Appearance | White powder |
| Impurity A | Not detected |
| Impurity B | 0.08% |
| Impurity C | <0.05% |
| Impurity D | 0.16% |
| Total Impurities | 0.3% |
| Sterility | Sterile |

The sample complies with USP specification

Example 5

One sample of micronised Brinzolamide (100 g) USP grade was packed under vacuum and under controlled atmosphere (helium) in LDPE liner inside a double Barrier Composite Foil (Polyester, Aluminium, HDPE), the material was exposed to a radiation of 25 KGy packed in dry ice at −78° C. The material was tested according to USP, details about appearance of the powder, related substances and sterility were given in Table 5.

TABLE 5

| Test | 25 KGy, −78° C., $He_2$, |
|---|---|
| Appearance | White powder |
| Impurity A | Not detected |
| Impurity B | 0.06% |
| Impurity C | <0.05% |
| Impurity D | 0.11% |
| Total Impurities | 0.2% |
| Sterility | Sterile |

The sample complies with USP specification

The invention claimed is:

1. A process for preparation of a sterile Brinzolamide, the process comprising:
    placing a bulk powder of Brinzolamide inside a bag made of polyethylene;
    creating a protective atmosphere that replaces ambient air in the bag made of polyethylene;
    sealing the bag made of polyethylene;
    placing the sealed bag made of polyethylene inside a bag made of oxygen-and-humidity-proof high-barrier material, wherein the high barrier material is polylaminated aluminium or metallized foil coupled with polyester and polypropylene or polyethylene;
    creating a protective atmosphere that replaces ambient air in the bag made of oxygen-and-humidity-proof high-barrier material;
    wherein the protective atmosphere that replaces ambient air in the bag made of polyethylene and in the bag made of oxygen-and-humidity-proof high-barrier material is selected from vacuum, argon, nitrogen, and helium;
    sealing the bag made of oxygen-and-humidity-proof high-barrier material; and
    performing terminal gamma-ray sterilization treatment on the bulk powder of Brinzolamide.

2. The process according to claim 1, wherein the gamma-ray sterilization treatment is carried out with a radiation of 25 kGy.

3. The process according to claim 1, wherein the gamma-ray sterilization treatment is carried out on the Brinzolamide powder packed under vacuum.

4. The process according to claim 1, wherein the gamma-ray sterilization treatment is carried out on the Brinzolamide powder packed in nitrogen or helium atmosphere.

5. The process according to claim 1, wherein the gamma-ray sterilization treatment is carried out at room temperature or below zero up to −78° C.

6. The process according to claim 2, wherein the gamma-ray, sterilization treatment is carried out at −78° C., with a radiation of 25 kGy and on the Brinzolamide powder packed in helium atmosphere.

* * * * *